(12) United States Patent
Pandey

(10) Patent No.: US 9,909,983 B2
(45) Date of Patent: Mar. 6, 2018

(54) METHOD AND APPARATUS FOR IMPROVING MEASUREMENT ACCURACY

(71) Applicant: ASML Netherlands B.V., Veldhoven (NL)

(72) Inventor: Nitesh Pandey, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/013,348

(22) Filed: Feb. 2, 2016

(65) Prior Publication Data

US 2016/0231241 A1    Aug. 11, 2016

(30) Foreign Application Priority Data

Feb. 6, 2015    (EP) ..................................... 15154216

(51) Int. Cl.
| | | |
|---|---|---|
| *G01B 9/02* | (2006.01) | |
| *G01N 21/47* | (2006.01) | |
| *G03F 7/20* | (2006.01) | |

(52) U.S. Cl.
CPC ..... *G01N 21/4788* (2013.01); *G03F 7/70625* (2013.01); *G03F 7/70633* (2013.01); *G03F 7/70641* (2013.01); *G03F 7/70941* (2013.01)

(58) Field of Classification Search
CPC .. G01B 9/02083; G01B 9/02084; G03F 7/706
See application file for complete search history.

(56) References Cited

U.S. PATENT DOCUMENTS

| | | |
|---|---|---|
| 7,502,117 B1 | 3/2009 | Wickholm |
| 2005/0046864 A1 | 3/2005 | Millerd et al. |
| 2005/0078318 A1* | 4/2005 | De Groot ........... G01B 11/0675 356/497 |
| 2005/0105100 A1 | 5/2005 | Swindal |

(Continued)

FOREIGN PATENT DOCUMENTS

| | | |
|---|---|---|
| EP | 0244781 A2 | 11/1987 |
| EP | 2416122 A1 | 2/2012 |

(Continued)

OTHER PUBLICATIONS

"Fast Fourier Transform", Wikipedia. Downloaded from <http://en.wikipedia.org/wiki/Fast_Fourier_transform> on Dec. 12, 2014; 11 pages.

(Continued)

*Primary Examiner* — Jonathan Hansen
(74) *Attorney, Agent, or Firm* — Sterne, Kessler, Goldstein & Fox, P.L.L.C.

(57) ABSTRACT

An optical system (10) includes an arrangement for splitting a source beam into a measurement beam and a reference beam. The reference beam is reflected off a reflective element (42) which mounted on a delay line (44). A target (35) scatters the radiation from the measurement beam. The scattered radiation and the reference beam are brought to interfere on a detector (40) by calibrating the delay line (44). The detected interference pattern is Fourier-transformed and filtered to select a region of interest around a side-band of the Fourier-transformed interference pattern in order to remove noise caused by stray radiation that hits the detector.

20 Claims, 6 Drawing Sheets

(56) References Cited

U.S. PATENT DOCUMENTS

| | | |
|---|---|---|
| 2006/0033921 A1 | 2/2006 | Den Boef et al. |
| 2006/0098895 A1 | 5/2006 | Westphal |
| 2008/0111996 A1 | 5/2008 | Takeda et al. |
| 2010/0201963 A1 | 8/2010 | Cramer et al. |
| 2010/0328655 A1 | 12/2010 | Den Boef |
| 2011/0007323 A1 | 1/2011 | De Groot et al. |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0044470 A1 | 2/2012 | Smilde et al. |
| 2012/0075601 A1 | 3/2012 | Den Boef et al. |
| 2012/0123581 A1 | 5/2012 | Smilde et al. |
| 2012/0200901 A1* | 8/2012 | Dubois .................. G02B 21/00 359/15 |
| 2013/0070251 A1* | 3/2013 | Das ...................... G02B 21/365 356/457 |
| 2013/0258310 A1 | 10/2013 | Smilde et al. |
| 2013/0271740 A1 | 10/2013 | Quintanilha |
| 2014/0139814 A1 | 5/2014 | Cramer et al. |
| 2015/0346605 A1 | 12/2015 | Den Boef et al. |

FOREIGN PATENT DOCUMENTS

| | | |
|---|---|---|
| WO | WO 2012/126718 A1 | 9/2012 |
| WO | WO 2013/178422 A1 | 12/2013 |
| WO | WO 2014/082938 A1 | 6/2014 |
| WO | WO 2015/090838 A1 | 6/2015 |

OTHER PUBLICATIONS

"Retroreflector", Wikipedia. Downloaded from <http://en.wikipedia.org/wiki/Retroreflector> on Dec. 17, 2014; 9 pages.

Lehar, S., "An Intuitive Explanation of Fourier Theory", Boston University. Downloaded from <http://cns-alumni.bu.edu/~slehar/fourier/fourier.html> on Feb. 4, 2015; 9 pages.

Schlotter, B., "Fourier Transform Holography: Single Shot Imaginig on a Photon Budget", Stanford University, Stanford Synchroton Radiation Laboratory; 51 pages.

International Search Report and Written Opinion if the International Searching Authority directed to related International Patent Application No. PCT/EP2016/051080, dated Jun. 15, 2016; 11 pages.

* cited by examiner

METHOD AND APPARATUS FOR IMPROVING MEASUREMENT ACCURACY

CROSS REFERENCE TO RELATED APPLICATIONS

EP Application 15154216.4 is incorporated by reference herein in its entirety.

FIELD

The present invention relates to a method for improving measurement accuracy in an optical system. The invention may be applied for example in inspection apparatus and lithographic apparatuses usable, for example, in the manufacture of devices by lithographic techniques.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 20120126718. Methods and scatterometers are also disclosed in US20110027704A1, US2006033921A1 and US2010201963A1. The targets used by such scatterometers are relatively large, e.g., 40 µm by 40 µm, gratings and the measurement beam generates an illumination spot that is smaller than the grating (i.e., the grating is underfilled). In addition to scatterometry to determine parameters of a structure made in one patterning step, the methods and apparatus can be applied to perform diffraction-based overlay measurements.

Diffraction-based overlay metrology using dark-field image detection of the diffraction orders enables overlay measurements on smaller targets. These targets can be smaller than the illumination spot and may be surrounded by product structures on a wafer. Multiple targets can be measured in one image. Examples of dark-field imaging metrology can be found in international patent applications US2010328655 A1 and US2011069292 A1 which documents are hereby incorporated by reference in their entirety. Further developments of the technique have been described in published patent publications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference.

However, although the invention is described in the context of an inspection apparatus, the invention is not limited in application to any particular type of inspection apparatus, or even to inspection apparatuses generally. The invention is in principle applicable to any apparatus wherein periodic measurement targets are utilized. Exemplary applications include, without limitation: measuring overlay in an inspection apparatus; focus control; measurement of critical dimension (CD); or measuring the form of a target (such as SWA or bottom tilt).

A common problem in inspection apparatuses and other optical systems is one of measurement accuracy, which is in part determined by the accuracy of the images obtained during the measurement. The image accuracy is in turn dependent on the optical system used to obtain the images. A major source of inaccuracy in images obtained from a given optical system, such as an inspection apparatus, is optical noise, e.g. stray radiation which enters the system and hits the detectors or cameras during measurements.

Stray radiation reduces the quality, and by extension the accuracy, of the detected images, and by extension the optical measurement system. This reduces the precision of the lithographic apparatus, thereby negatively impacting the precision of components produced by the apparatus, in particular in systems where the detected radiation intensities are very low. It is, therefore, desirable to remove or reduce the amount of stray radiation in an optical system, particularly an optical measurement system in a lithographic apparatus.

One source of stray radiation in an inspection apparatus is radiation being reflected from surfaces of components that are part of the optical system, e.g. tiny imperfections on the surfaces of optical components (such as mirrors or aperture stops) as well as multiple reflections off optical surfaces such as lenses. This is particularly problematic in complex lens systems, such as used in lithographic apparatuses, which contain a large number of lenses. In such systems, even a small fraction of reflected stray radiation may compound into a significant source of stray radiation and optical noise. A further source of stray radiation is radiation reflected from interior surfaces of the apparatus that are not part of the optical system, e.g. from other optical systems used for other purposes that are also housed within the inspection apparatus. A further source of stray radiation is radiation reflected off parts of the substrate other than the measurement target itself (e.g. nearby components on the substrate). Yet a further source of stray radiation is foreign particles within the system, such as microscopic dust particles floating inside the apparatus or on an optical surface.

Stray radiation can broadly be classed into two types:

a. directional stray radiation, which is e.g. caused by radiation being reflected multiple times from various surfaces either part of the optical system or not part of the optical system. For example, stray radiation reflections from glass surfaces in the optical system, such as lenses used to shape the beams, can be considered to be directional stray radiation.

b. non-directional stray radiation, which is radiation that is randomly scattered by rough surfaces, or by foreign particles, such as dust, inside the apparatus.

Conventionally, stray radiation in an optical system is reduced by use of suitable anti-reflection coatings, as well as use of apertures and stops at appropriate places in the optical path of the system. However, anti-reflection coatings may only reduce the amount of stray radiation, rather than remove it entirely. In complex optical systems, such as lens systems used in lithographic apparatuses, the compound effect of stray radiation being reflected off each lens surface may be significant. Furthermore, as described above, aperture stops may themselves be sources of stray radiation due to small imperfections in their surfaces, for example due to imperfections in their manufacturing process or by having become damaged.

SUMMARY

The inventors have recognized that stray radiation, which hits a detector in an optical system, has travelled a different optical path, and hence a different optical path length, than scattered radiation from a measurement beam that hits the same detector after having been scattered by a measurement target.

In particular, the inventors have recognized that by creating an interference pattern between a measurement beam and a reference beam, radiation which is not coherent with the measurement beam and/or the reference beam will not interfere with either of these beams, and will therefore only add to the DC component of the interferogram. By removing the DC component from the interferogram, the stray radiation can be effectively filtered out without affecting the quality of the measurement beam.

In accordance with a first embodiment of the invention, there is therefore provided a method of inspecting a substrate, comprising: splitting a source beam of radiation emitted by a radiation source into a measurement beam and a reference beam; illuminating a target area on a substrate with the measurement beam; collecting at least a portion of scattered radiation from the target area and delivering the collected scattered radiation to a detector; delivering the reference beam to the detector so as to interfere with the collected scattered radiation and form an interference pattern at the detector; modifying the interference pattern; and determining a parameter of the target based on the interference pattern.

In accordance with a further embodiment of the invention, there is provided a method of measuring a parameter of a lithographic process, comprising: splitting a source beam of radiation emitted by a radiation source into a measurement beam and a reference beam; illuminating a target area on a substrate with the measurement beam; collecting at least a portion of scattered radiation from the target area and delivering the collected scattered radiation to a detector; delivering the reference beam to the detector so as to interfere with the collected scattered radiation and form an interference pattern at the detector; modifying the interference pattern; and determining the parameter of the target based on the interference pattern.

In accordance with yet a further embodiment of the invention, there is provided a method of filtering stray radiation, the method comprising: receiving incoming radiation at a detector, the incoming radiation comprising scattered radiation from a target to be measured; causing part of the incoming radiation to interfere with a reference beam to create an interference pattern; and filtering the incoming radiation to remove the part of the incoming radiation which does not interfere with the reference beam.

In accordance with a further embodiment of the invention, there is also provided an apparatus comprising means for carrying out any one of the aforementioned methods.

In accordance with a further embodiment of the invention, there is additionally provided a computer program product containing one or more sequences of machine-readable instructions for causing a programmable data processor to perform any of the aforementioned methods.

It should be noted, that the embodiments of the invention as described above, and in the following, are applicable in any apparatus wherein optical measurements are performed. In particular, the embodiments are applicable to any methods or apparatuses which form part of a lithographic process, wherein optical measurements are performed on periodic targets (such as diffraction gratings) are used. Exemplary applications include, without limitation: measuring overlay in an inspection apparatus; focus control; measurement of critical dimension (CD); or measuring the form of a target (such as side wall angle (SWA) or bottom tilt). In exemplary applications, the parameter determined includes, without limitation, overlay, CD, focus, SWA or bottom tilt.

These and further features and advantages of the invention will be apparent to the skilled reader from a consideration of the detailed description of examples that follows.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
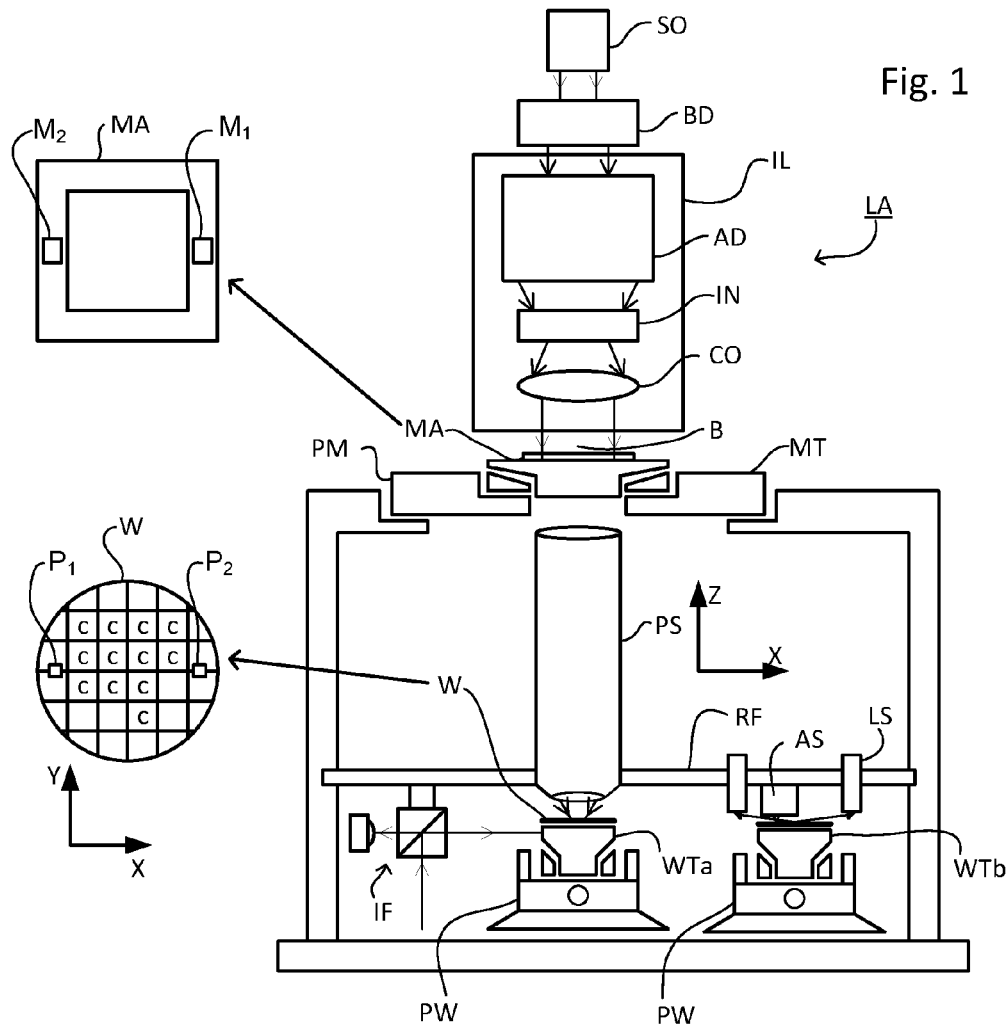
FIG. 1 depicts a lithographic apparatus according to an embodiment of the invention.

FIG. 1 schematically depicts a lithographic apparatus. The apparatus comprises:
- an illumination system (illuminator) IL configured to condition a radiation beam B (e.g. UV radiation or DUV radiation).
- a support structure (e.g. a mask table) MT constructed to support a patterning device (e.g. a mask) MA and connected to a first positioner PM configured to accurately position the patterning device in accordance with certain parameters;
- a substrate table (e.g. a wafer table) WT constructed to hold a substrate (e.g. a resist-coated wafer) W and connected to a second positioner PW configured to accurately position the substrate in accordance with certain parameters; and
- a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan.

In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
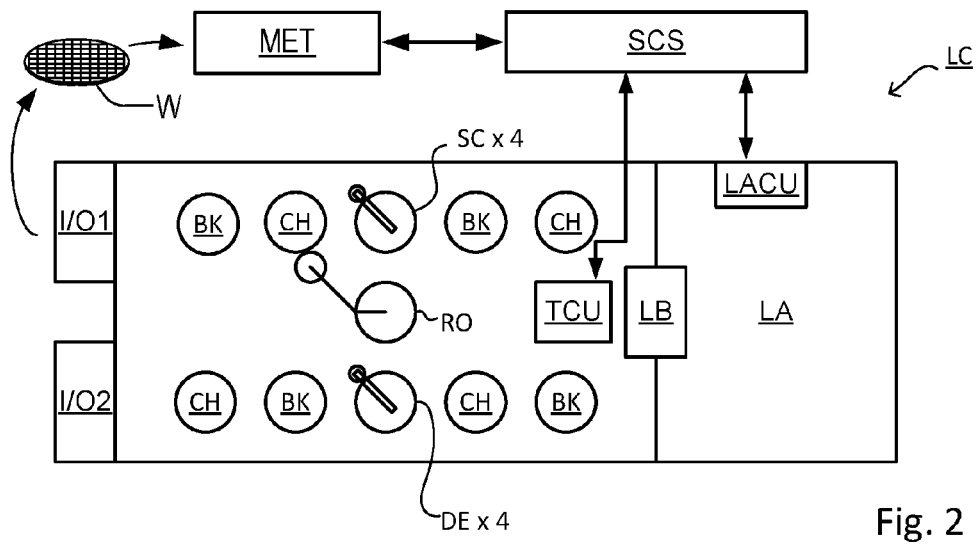
FIG. 2 depicts a lithographic cell or cluster incorporating the apparatus of FIG. 1.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
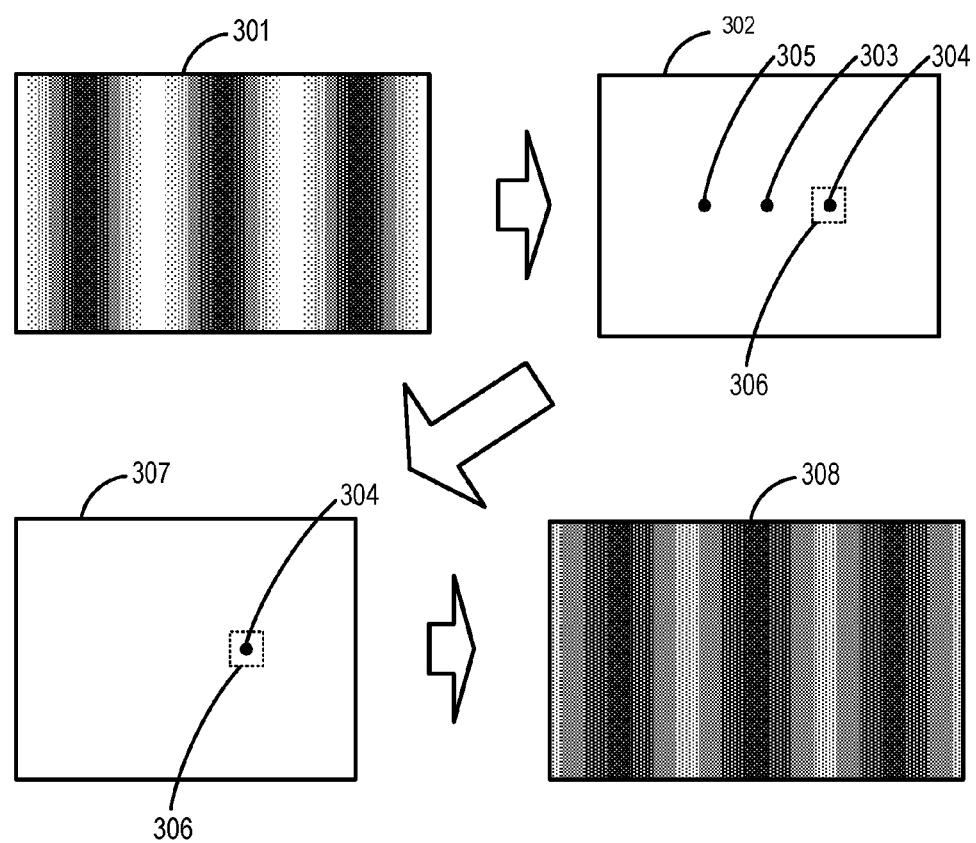
FIG. 3 illustrates schematically a measurement principle according to the invention.

The principle of the invention will now be described with reference to FIG. 3. As explained above, the inventors have realized that stray radiation travels along a different optical path than a measurement beam. In the following, the term measurement beam may be used to refer to the incident measurement beam, which propagates from the radiation source to the measurement target, as well as to the scattered radiation, which is comprised of the portion of the incident measurement beam reflected or scattered by the measurement target and received at a detector.

A radiation source emits a source beam, which can be split into a measurement beam and a reference beam. The incident measurement beam propagates from the radiation source to a measurement target along a well-defined optical path with a known optical path length. Similarly, scattered radiation propagates from the measurement target to a detector along a well-defined optical path with a known optical path length. However, stray radiation will generally not travel from the radiation source to the detector along an optical path with a similar, much less identical, optical path length to the optical path of the measurement beam. Hence, the scattered radiation will generally not be coherent with the measurement beam, as will now be explained.

By matching the optical path length of the reference beam with that of the measurement beam, an interference pattern is generated at the detector in a manner known in the art. FIG. 3 shows an exemplary interference pattern (301). It will, of course, be appreciated that the pattern consists of a simple sinusoidal variation for purposes of the example only, and that interference patterns in reality will be more complex than this. An interference pattern for radiation with a center wavelength $\lambda_0$ can generally be described by the following equation:

$$I(\lambda_0) = |A|^2 + |A_r|^2 + 2|A||A_r|\cos\left(\frac{2\pi\Delta L}{\lambda_0} - \alpha \cdot r\right) \quad (1)$$

A is the two-dimensional representation of the complex amplitude of the image and $A_r$ is the complex amplitude distribution of the reference beam. $\Delta L$ is the optical path length difference between the signal beam and the reference beam, $\alpha$ is the direction of propagation of the reference beam, and r is the position vector of the camera pixels.

For a radiation source, which emits radiation with a particular spectral width $\Delta\lambda$, the intensity distribution of the resulting interference pattern can be described by the following equation:

$$I_{tot} = \int_{\lambda_0 - \frac{\Delta\lambda}{2}}^{\lambda_0 + \frac{\Delta\lambda}{2}} |A|^2 + |A_r|^2 + 2|A||A_r|\cos\left(\frac{2\pi\Delta L}{\lambda_0} - \alpha \cdot r\right) d\lambda \quad (2)$$

$$= \Delta\lambda(|A|^2 + |A_r|^2) + 2|A||A_r|\Delta\lambda \frac{\sin\left(\frac{\pi\Delta L\Delta\lambda}{\lambda_0^2}\right)}{\left(\frac{\pi\Delta L\Delta\lambda}{\lambda_0^2}\right)} \cos\left(\frac{2\pi\Delta L}{\lambda_0} - \alpha \cdot r\right) \quad (3)$$

It follows from equations (2) and (3) that the modulation of the interference pattern (301) is largest when the optical path length difference is zero (i.e. $\Delta L=0$). It further follows that the interference pattern is only visible when the optical path length difference is $\Delta L < \lambda_0^2/\Delta\lambda$. In other terms, if interference fringes are visible, the optical path length difference of the signal and reference beams is smaller than $\lambda_0^2/\Delta\lambda$. This may be referred to as the 'coherence length' of the radiation. Thus, if stray radiation that hits the detector has travelled an optical path length that differs from the measurement beam by more than this optical path length difference, i.e. if the stray radiation is not coherent with the measurement beam, it will not interfere with the measurement beam but will only add to the DC component of the interferogram. This effect is known in the art as 'coherence gating'. Since it is possible that stray radiation may be coherent with the measurement beam, it is therefore generally advantageous to make the coherence length as short as possible. This can, for example, be done by increasing the spectral width of the radiation source.

As an example, a radiation source, which has a center wavelength $\lambda_0$ of 600 nm and a spectral width of $\Delta\lambda=30$ nm, has a coherence length of 12 μm. Exemplary light sources include, but are not limited to, super-luminescent diodes or white light filtered with a bandpass filter of the appropriate passband width.

Since the stray radiation does not interfere with the measurement beam, and only contributes to the DC component of the interference pattern, it can be removed by an appropriate filtering technique.

One such technique involves carrying out a Fourier Transformation of the interferogram. FIG. 3 shows a Fourier-transformed pattern (302) which corresponds to the interference pattern (301). In a manner known in the art, a sinusoid pattern, Fourier-transforms into a central dot (303) and right (304) and left (305) dots (which are sometimes referred to as 'side-bands'). The central dot represents the DC component of the interference pattern (301), i.e. the background level of the pattern. The right and left dots respectively represent the frequency component of the interference pattern and its conjugate.

To filter out the DC component, a Region of Interest (306) is selected around the right side-band (304). It should be noted that it would be equally possible to select the left side-band (305), or indeed to select both side-bands. Upon selecting the Region of Interest, everything outside this region is zeroed or otherwise removed to create a modified Fourier-transformed pattern (307). An inverse Fourier-transformation is then performed on the modified pattern, which results in a filtered interference pattern (308). As can be seen, the intensity of the fringes is lower than the original interference pattern (301) after the removal of the DC component.

Figure 4:
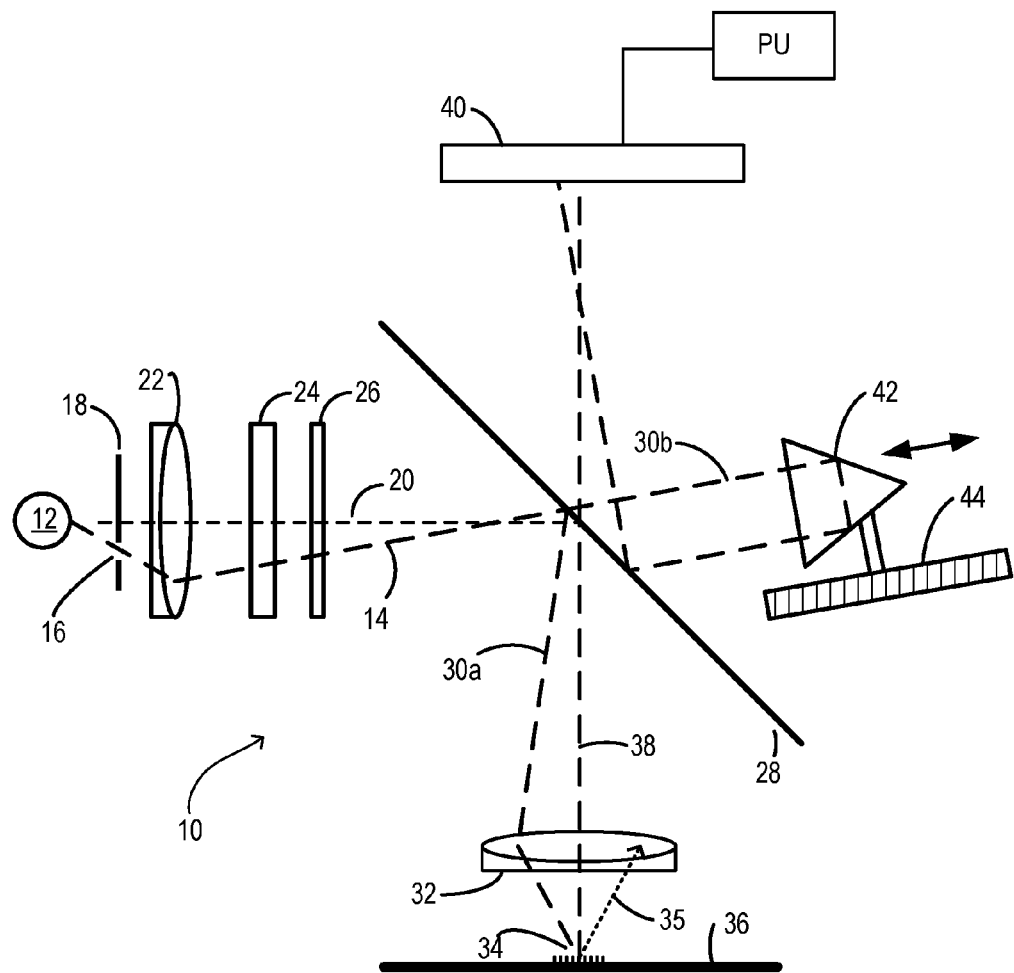
FIG. 4 depicts schematically an apparatus for carrying out the invention.

FIG. 4 schematically depicts an optical system (10) in accordance with an embodiment of the invention. A radiation source (12) emits a source beam (14) with a pre-defined emission spectrum. In one embodiment, the radiation source emits visible radiation and has a spectral width of 20-40 nm, although the skilled person would appreciate that radiation sources with other spectral widths could equally well be used. Examples of other possible radiation sources include (but are not limited to) white light sources (such as a Xenon lamps), laser produced plasma light sources, broadband lasers or single wavelength lasers.

The source beam (14) passes through an aperture (16) of an aperture stop or similar component (18). The aperture is offset from the optical axis (20) of the aperture stop, thereby creating an 'off-axis' interferometer. The radiation optionally passes through one or more further optical elements (22, 24, 26), such as lenses, optical filters, spatial light modulators, SLMs, or apertures. These optical elements may help shape or filter the source beam (14) in a desired manner.

The source beam hits a partially reflective surface of a beam splitter (28). This splits the source beam into a measurement beam (30a), which consists of the portion of the source beam (14) that is reflected by the partially reflective surface, and a reference beam (30b), which consists of the portion of the source beam (14) that is transmitted by the partially reflective surface. The measurement beam then passes through a lens element (32) and hits a target (34) on a target substrate (36). The target scatters at least a portion of the measurement beam. The properties of the scattered radiation (38) depends on the target (34). In the present embodiment, the target consists of a diffraction grating, which forms the scattered radiation into diffraction orders in a known manner. It will, of course, be appreciated that other forms of targets, each with particular reflection or scattering properties, could equally well be used. It will also be appreciated that the choice of target to be used on a given substrate is dependent on the particular type of measurement or application. Thus, if for example the overlay error of a substrate is measured, one particular target, with a particular set of radiation scattering properties, may be used, whilst different targets, with different radiation scattering properties, may be used for measuring CD or SWA.

In the present embodiment, the first order diffracted radiation passes through the lens element (32), through the beam splitter (28) and hits a detector (40). The remaining diffraction orders (35) of the scattered radiation are not used in the exemplary measurement, and are removed from the optical path in a convenient manner.

The reference beam (30b) is completely reflected by a reflective element (42). The reflective element could, for example, be a retroreflector. The reflective element is mounted on a so-called 'delay line' (44), which allows the reflective element to be moved in order to increase or decrease the optical path length of the reference beam (30b) so as to tune the reference beam to the measurement and to increase the contrast of the interference pattern at the detector. The frequency and orientation of the fringes of the interference pattern can be adjusted by rotating the reflective element. Adjusting the frequency of the fringes is important because the fringe frequency that can be detected is limited by the properties of the detector (e.g the pixel pitch of a camera, in which case the fringe frequency should not be higher than half the pixel pitch of the camera).

The reflected reference beam is then reflected by the beam splitter (28) and hits the detector (40).

If the scattered radiation is coherent with the reflected reference beam, i.e. if the optical path length difference is less than $\Delta L < \lambda_0^2/\Delta\lambda$, the scattered radiation will interfere with the reference beam on the surface of the detector, thereby creating an interference pattern on the detector. The interference pattern is detected by the detector and sent to a processing unit (PU) for processing and filtering.

A method in accordance with an embodiment of the invention will now be described with reference to FIG. 5. The reference numerals in this figure refer to the following steps, each of which will be explained in more detail in the following:

501: Generating a source beam;
502: Splitting the source beam;
503: Illuminating a target area;
504: Collecting scattered radiation;
505: Delivering scattered radiation to detector;
506: Calibrating reference beam;
507: Delivering reference beam to detector;
508: Modifying interference pattern; and
509: Determining parameter.

Figure 5:
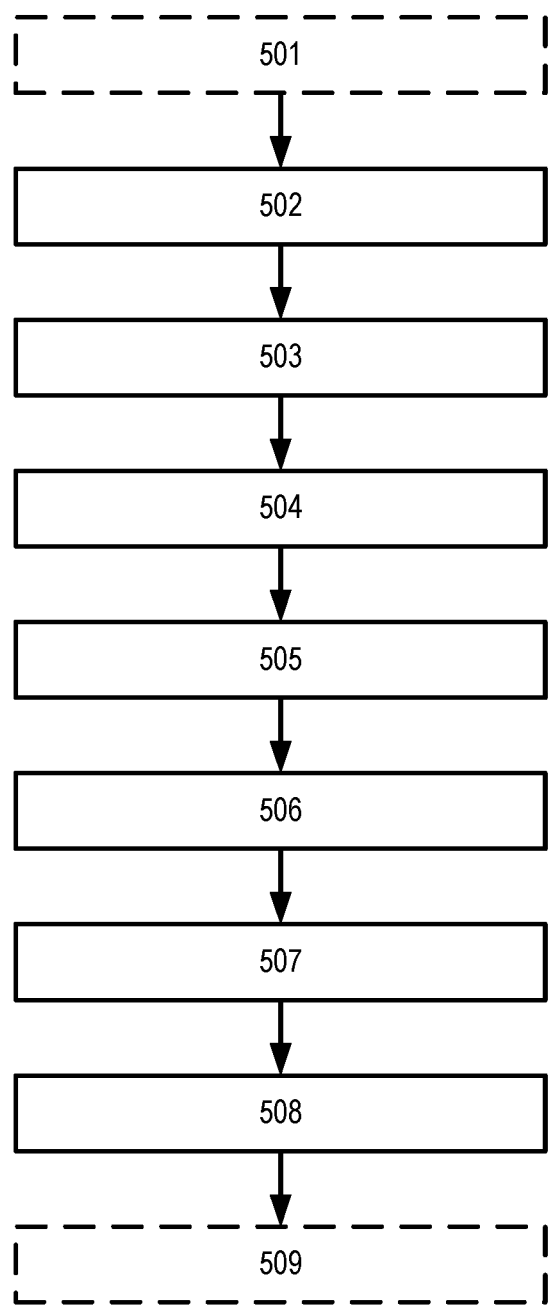
FIG. 5 is a diagram of a method for measuring radiation according to one embodiment of the invention.

It is to be noted that, although the above steps are depicted in FIG. 5 and discussed below in a particular order, some of these steps may be performed in a different order, or may be performed simultaneously.

In an optional first step, a radiation source generates (501) a source beam of radiation. The source beam can be generated by a radiation source internal to the apparatus of the invention, or it can be generated externally to the apparatus.

The source beam is split (502) into a measurement beam and a reference beam by a beamsplitter, as described above with reference to FIG. 4.

The measurement beam illuminates (503) a measurement target on a target substrate. The target reflects or scatters the measurement beam according to its particular properties. The properties of measurement targets are well known in the art and allows measurement targets to be selected to achieve a desired effect. The scattered radiation is collected (504) in a suitable fashion and is delivered (505) to a detector by way of a suitable optical system.

A calibration system, such as a reflective element on a delay line, is used to calibrate (506) the reference beam. In the present embodiment, the reference beam is calibrated by adjusting the optical path length between the radiation source and the detector. The calibration is performed in order to maximise the contrast of the interference pattern at the detector.

The reference beam is then delivered (507) to the detector, where it interferes with the measurement beam as described above.

The detected interference pattern, after detection by the detector, can be modified (508) by a suitable processing unit, such as a computer. Based on the filtered interference pattern a parameter of the target may then be determined (509). As the influence of the stray radiation has been removed, the amount of optical noise in the interference pattern is reduced or eliminated. This, in turn improves the accuracy of the measurement which is carried out based on the modified interference pattern.

Figure 6:
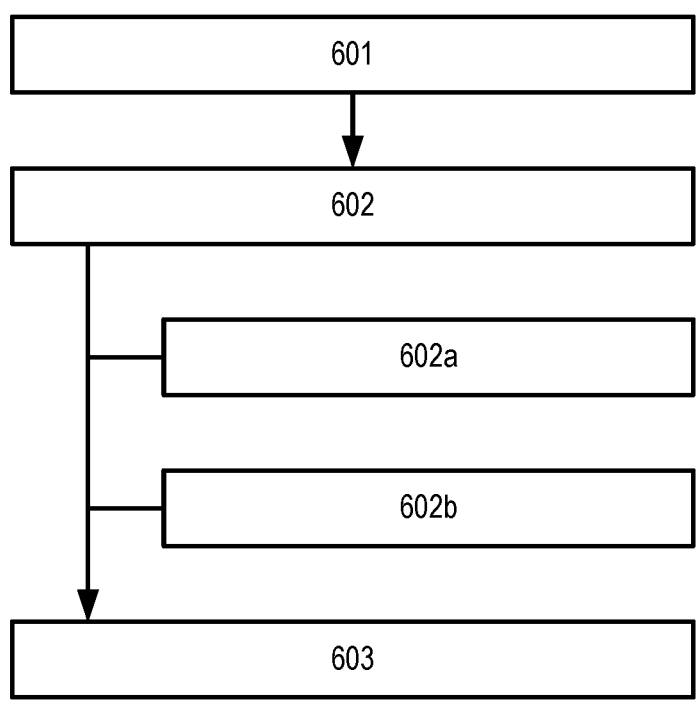
FIG. 6 illustrates the steps of filtering radiation received according to the method of FIG. 5.

FIG. 6 shows details of the modification step (508) of FIG. 5 according to one embodiment of the invention. In this embodiment, modifying the detected interference pattern consists of the following sub-steps:

601: Performing a Fourier transformation on the interference pattern;
602: Applying a filter to the Fourier-transformed interference pattern;
602a: Identifying a Region of Interest;
602b: Removing the pattern outside the Region of Interest; and
603: Performing an inverse Fourier transformation on the remaining Fourier-transformed pattern to obtain a modified pattern.

After the interference pattern has been picked up by the detector, a processing unit performs (601) a Fourier-transformation on the detected interference pattern to create a Fourier-transformed interference pattern. In the present embodiment, a Fast Fourier Transform algorithm (which is a specific method for implementing a Discrete Fourier Transform) is used by the processing unit, although other Fourier Transform algorithms exist and may be used if desired or advantageous.

A filter is then applied (602) to the Fourier-transformed interference pattern. The filtering process consists of a first step of identifying (602a) a Region of Interest (ROI). In the present embodiment, as described above, the ROI is one of the side-bands, specifically the right side-band. As is known in the art, one side-band of a Fourier-transform of a hologram or interferogram represents the Fourier spectrum of the complete image wave, and the other side-band represents its conjugate.

Subsequent to identifying the ROI, a second step of the filtering process is carried out. In the present embodiment, the second step of the filtering process consists of removing (602b) the part of the Fourier-transformed interference pattern that is located outside the ROI. Other types of filters could be used. If, for example, it is intended to only remove the central part of the Fourier-transformed interference pattern, a high-pass filter could be used.

An inverse Fourier-transform is then performed (603) on the pattern in the ROI to obtain the original image wave, i.e. an image of the target illuminated by the measurement beam.

Figure 7:
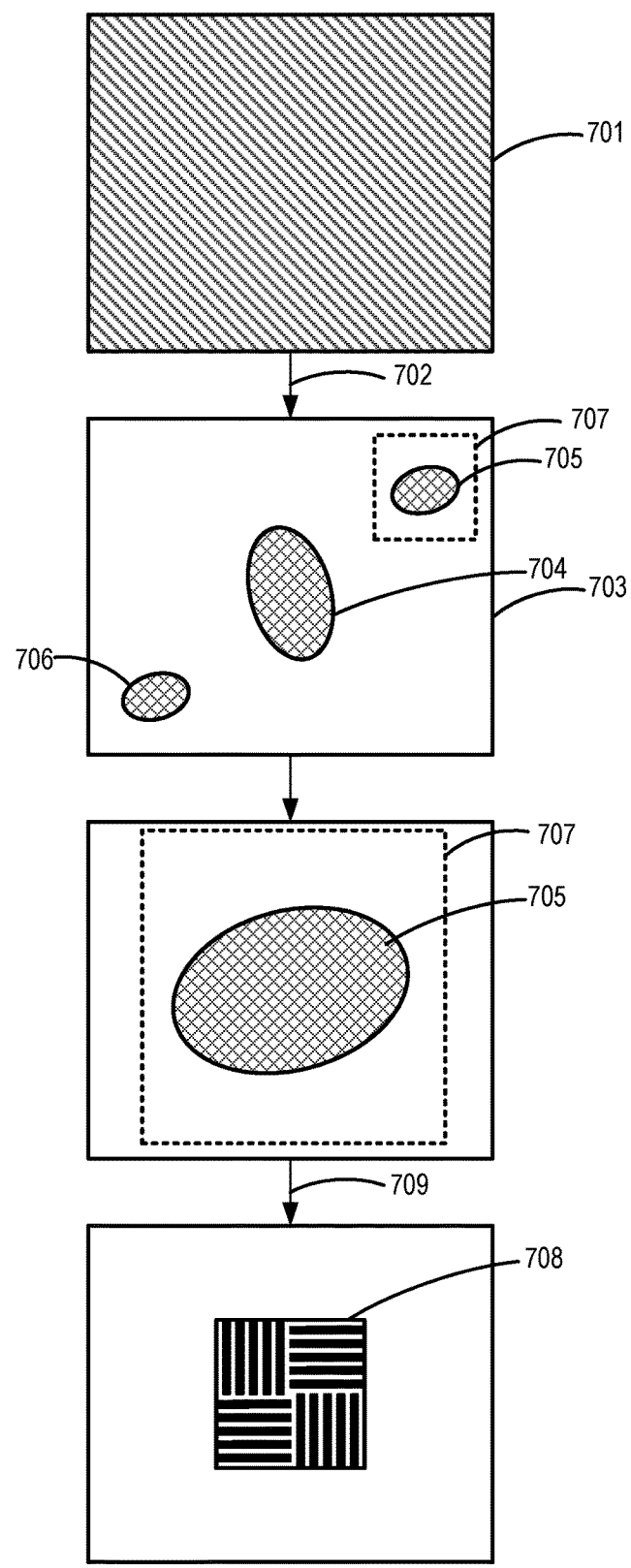
FIG. 7 shows schematically the methods steps of FIG. 6.

FIG. 7 shows a schematic depiction of an interference pattern (701) received at an image detector. As previously described, the interference pattern is caused by a reference beam interfering with scattered radiation reflected from a measurement target. The interference pattern is then Fourier-transformed (702) as described above, resulting in a Fourier-transformed pattern (703), which has a central part (704) and right and left side-bands (705, 706). The central part contains the DC component of the received radiation. This includes the contribution from any radiation that has been received, but which has not interfered with either the reference beam or the scattered radiation, such as stray radiation incident on the detector. Both side-bands represent the Fourier spectrum of the complete image wave. The left side-band (706) is the conjugate of the right side-band (705). The relative positions of the side-bands and the central part can be adjusted during the measurement process by adjusting the position and orientation of the reflective element as described with reference to FIG. 4. Hence, by adjusting the frequency of the interference fringes of the interference pattern, the position of the side-bands relative to the central part can be adjusted, e.g. to ensure they separate from the central part, thereby facilitating identification and selection of the side-bands during subsequent steps.

A ROI (707) is then selected. The ROI is centred on the right side-band (705), although, as explained, the left side-band (706) could equally well have been selected. Elimination of stray radiation is accomplished by removing the central part (704) of the Fourier-transformed pattern. The ROI can be selected manually, or it can be selected automatically by an algorithm implemented in the processing unit. For example, a pattern recognition algorithm can be used to detect the side-bands. Alternatively, a Chirp-Z transform can be used to extract the ROI.

After selecting the ROI, an inverse Fourier-transformation is performed (709). As the side-band represents the Fourier spectrum of the complete image wave, performing an inverse Fourier-transformation will yield the original image of the target (708). Based on the obtained image of the target, it is then possible to evaluate the parameter, such as (but not limited to) overlay error, CD, focus, SWA or bottom tilt.

CONCLUSION

The method and associated apparatus disclosed herein enable at least one or more of the following benefits.

Stray radiation and spurious reflections may be completely filtered, since only radiation which meets the coherence requirements interferes with the signal beam, and therefore the measurement results. Any other radiation merely adds to the DC component of the resulting interferogram.

The reference arm, which contains the optical elements for the reference beam, can be added to existing apparatuses. Hence, the optics of existing lithographic apparatuses can be kept intact, thereby enabling these to be upgraded rather than having to be replaced.

The system is backward compatible when the reference arm can be switched off

The signals from weak gratings can be interferometrically boosted by using a stronger reference beam.

The interferometric signal is also focus sensitive and can be used for focusing.

Although specific reference may be made in this disclosure to the use of coherence gating in inspection apparatuses such as scatterometers, it should be understood that the disclosed arrangements may have application in other types of functional apparatuses, as mentioned already above.

Although specific reference may be made in this text to the use of inspection apparatus in the manufacture of ICs, it should be understood that the inspection apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

Further embodiments according to the invention are provided in below numbered clauses:

1. A method of inspecting a substrate, the method comprising: splitting a source beam of radiation emitted by a radiation source into a measurement beam and a reference beam;

illuminating a target area on a substrate with the measurement beam;

collecting at least a portion of scattered radiation from the target area and delivering the collected scattered radiation to a detector;

delivering the reference beam to the detector so as to interfere with the collected scattered radiation and form an interference pattern at the detector;

modifying the interference pattern; and determining a parameter of the target based on the interference pattern.

2. A method according to clause 1, wherein the modifying includes removing a DC component of the interference pattern.

3. A method according to clause 1 or 2 wherein the modifying comprises performing a Fourier transformation of the interference pattern.

4. A method according to clause 3, wherein the modifying further comprises applying a filter to at least part of the Fourier-transformed interference pattern.

5. A method according to clause 4, wherein applying a filter comprises identifying a region of interest in the Fourier-transformed interference pattern.

6. A method according to clause 5, further comprising performing an operation on a portion of the Fourier-transformed interference pattern which is outside the region of interest.

7. A method according to clause 6, wherein the operation comprises zeroing the portion of the Fourier-transformed interference pattern which is outside the region of interest 8. A method according to any of clauses 3 to 7, wherein modifying the interference pattern further comprises performing an inverse Fourier transformation on the filtered Fourier-transformed interference pattern.

9. A method according to any previous clause, wherein delivering the reference beam comprises adjusting an optical path difference between the scattered radiation and the reference beam where they interfere at the detector.

10. A method according to clause 9, comprising adjusting the optical path difference to be smaller than a threshold value.

11. A method according to clause 10, wherein the threshold value is based on at least one of the central wavelength of the source beam and the spectral bandwidth of the source beam.

12. A method according to clause 11, wherein the threshold value is the coherence length of the source beam.

13. A method of measuring a parameter of a lithographic process, the method comprising:
splitting a source beam of radiation emitted by a radiation source into a measurement beam and a reference beam;
illuminating a target area on a substrate with the measurement beam;
collecting at least a portion of scattered radiation from the target area and delivering the collected scattered radiation to a detector;
delivering the reference beam to the detector so as to interfere with the collected scattered radiation and form an interference pattern at the detector;
modifying the interference pattern; and
determining a parameter based on the interference pattern.

14. A method according to clause 13, wherein the modifying includes removing a DC component of the interference pattern.

15. A method according to clause 13 or 14 wherein the modifying comprises performing a Fourier transformation of the interference pattern.

16. A method according to clause 15, wherein the modifying further comprises applying a filter to at least part of the Fourier-transformed interference pattern.

17. A method according to clause 16, wherein applying a filter comprises identifying a region of interest in the Fourier-transformed interference pattern.

18. A method according to clause 17, further comprising performing an operation on a portion of the Fourier-transformed interference pattern which is outside the region of interest.

19. A method according to clause 18, wherein the operation comprises zeroing the portion of the Fourier-transformed interference pattern which is outside the region of interest 20. A method according to any of clauses 15 to 19, wherein modifying the interference pattern further comprises performing an inverse Fourier transformation on the filtered Fourier-transformed interference pattern.

21. A method according to any of clauses 13 to 20, wherein delivering the reference beam comprises adjusting an optical path difference between the scattered radiation and the reference beam where they interfere at the detector.

22. A method according to clause 21, comprising adjusting the optical path difference to be smaller than a threshold value.

23. A method according to clause 22, wherein the threshold value is based on at least one of the central wavelength of the source beam and the spectral bandwidth of the source beam.

24. A method according to clause 23, wherein the threshold value is the coherence length of the source beam.

25. A method of filtering stray radiation, the method comprising:
receiving incoming radiation at a detector, the incoming radiation comprising scattered radiation from a target to be measured;
causing part of the incoming radiation to interfere with a reference beam to create an interference pattern; and
filtering the incoming radiation to remove the part of the incoming radiation which does not interfere with the reference beam.

26. A method according to clause 25, wherein the filtering comprises removing a first part of the incoming radiation, wherein the first part has an optical path difference between the optical path length of the first part and the scattered radiation that is larger than the threshold value.

27. A method according to clause 25 or 26, wherein the filtering includes removing a DC component of the interference pattern.

28. A method according to any of clauses 25 to 27, wherein the filtering comprises performing a Fourier transformation of the interference pattern.

29. A method according to clause 28, wherein the filtering further comprises applying a filter to at least part of the Fourier-transformed interference pattern.

30. A method according to clause 29, wherein applying a filter comprises identifying a region of interest in the Fourier-transformed interference pattern.

31. A method according to clause 30, further comprising performing an operation on a portion of the Fourier-transformed interference pattern which is outside the region of interest.

32. A method according to clause 31, wherein the operation comprises zeroing the portion of the Fourier-transformed interference pattern which is outside the region of interest 33. A method according to any of clauses 28 to 32, wherein the filtering further comprises performing an inverse Fourier transformation on the filtered Fourier-transformed interference pattern.

34. A method according to any of clauses 25 to 33, wherein causing part the incoming radiation to interfere with the reference beam comprises:
adjusting the optical path length difference between the scattered radiation and the reference beam to be smaller than a threshold value.

35. A method according to clause 34, wherein the threshold value is based on at least one of the central wavelength of the source beam and the spectral bandwidth of the source beam.

36. A method according to clause 35, wherein the threshold value is the coherence length of the scattered radiation.

37. A method according to any previous clause, wherein the parameter is one of overlay error, critical dimension, focus, side wall angle or bottom tilt.

38. An apparatus comprising means for carrying out the method of any of clauses 1 to 37.

39. A computer program product containing one or more sequences of machine-readable instructions for causing a programmable data processor to perform the method of any of clauses 1 to 37.

While specific embodiments of the invention have been described above, it will be appreciated that the invention may be practiced otherwise than as described. Furthermore, parts of the apparatus may be implemented in the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:
1. A method of inspecting a substrate, the method comprising:

splitting a source beam of radiation emitted by a radiation source into a measurement beam and a reference beam, wherein the source beam passes through an aperture of an optical element and the aperture is offset from an optical axis of the optical element;

illuminating a target area on the substrate with the measurement beam;

collecting at least a portion of scattered radiation from the target area;

delivering the collected scattered radiation to a detector;

delivering the reference beam to the detector so as to interfere with the collected scattered radiation and form an interference pattern at the detector;

modifying the interference pattern; and determining a parameter of the target based on the modified interference pattern.

2. The method as claimed in claim 1, wherein the modifying includes removing a DC component of the interference pattern.

3. The method as claimed in claim 1, wherein the modifying comprises performing a Fourier transformation of the interference pattern.

4. The method as claimed in claim 3, wherein the modifying further comprises applying a filter to at least part of the Fourier-transformed interference pattern.

5. The method as claimed in claim 4, wherein the applying a filter comprises identifying a region of interest in the Fourier-transformed interference pattern.

6. The method as claimed in claim 4, wherein the modifying the interference pattern further comprises performing an inverse Fourier transformation on the filtered Fourier-transformed interference pattern.

7. The method according to claim 1, wherein the delivering the reference beam comprises adjusting an optical path difference between the scattered radiation and the reference beam where they interfere at the detector.

8. A method of measuring a parameter of a lithographic process, the method comprising:

splitting a source beam of radiation emitted by a radiation source into a measurement beam and a reference beam, wherein the source beam passes through an aperture of an optical element and the aperture is offset from an optical axis of the optical element;

illuminating a target area on a substrate with the measurement beam;

collecting at least a portion of scattered radiation from the target area;

delivering the collected scattered radiation to a detector;

delivering the reference beam to the detector so as to interfere with the collected scattered radiation and form an interference pattern at the detector;

modifying the interference pattern; and determining the parameter based on the modified interference pattern.

9. The method as claimed in claim 8, wherein the modifying includes removing a DC component of the interference pattern.

10. The method as claimed in claim 8, wherein the modifying comprises performing a Fourier transformation of the interference pattern.

11. The method as claimed in claim 10, wherein the modifying the interference pattern further comprises performing an inverse Fourier transformation on a filtered Fourier-transformed interference pattern.

12. The method according to claim 8, wherein the delivering the reference beam comprises adjusting an optical path difference between the scattered radiation and the reference beam where they interfere at the detector.

13. An off-axis interferometer, comprising:

an optical element comprising an aperture such that a source beam passes through the aperture, wherein the aperture is offset from an optical axis of the optical element;

a controller configured to:

receive incoming radiation, the incoming radiation comprising scattered radiation from a target to be measured, wherein the target is illuminated with a measurement beam generated from the source beam; and cause the incoming radiation to interfere with a reference beam of the off-axis interferometer to create an interference pattern, wherein the reference beam generated from the source beam; and a processor configured to filter the interference pattern to remove part of the incoming radiation which does not interfere with the reference beam.

14. The off-axis interferometer according to claim 13, wherein the processor is further configured to remove a first part of the incoming radiation, wherein the first part has an optical path difference between an optical path length of the first part and the scattered radiation that is larger than the threshold value.

15. The off-axis interferometer according to claim 13, wherein the processor is further configured to remove a DC component of the interference pattern.

16. The off-axis interferometer according to claim 15, wherein the processor is further configured to:

perform a Fourier transformation of the interference pattern;

apply a filter to the Fourier-transformed interference pattern; and perform an inverse Fourier transformation on the filtered Fourier-transformed interference pattern.

17. The off-axis interferometer according to claim 13, wherein the processor is further configured to adjust an optical path length difference between the scattered radiation and the reference beam to be smaller than a threshold value.

18. The method according to claim 1, wherein the parameter is one of overlay error, critical dimension, side wall angle or bottom tilt.

19. An apparatus comprising:

an optical element comprising an aperture such that a source beam passes through the aperture, wherein the aperture is offset from an optical axis of the optical element;

a beam splitter configured to split the source beam of radiation emitted by a radiation source into a measurement beam and a reference beam;

a detector configured to collect at least a portion of scattered radiation from a target area illuminated with the measurement beam;

an optical apparatus configured to direct the reference beam to the detector so as to interfere with the collected scattered radiation and form an interference pattern at the detector; and a processing device configured to modify the interference pattern and to determine a parameter of the target based on the modified interference pattern.

20. A computer-readable medium having instructions stored thereon that, when executed by at least one computing device, causes the at least one computing device to perform operations comprising:

splitting a source beam of radiation emitted by a radiation source into a measurement beam and a reference beam, wherein the source beam passes through an aperture of an optical element and the aperture is offset from an optical axis of the optical element;
illuminating a target area on a substrate with the measurement beam;
collecting at least a portion of scattered radiation from the target area;
delivering the collected scattered radiation to a detector;
delivering the reference beam to the detector so as to interfere with the collected scattered radiation and form an interference pattern at the detector;
modifying the interference pattern; and
determining a parameter of the target based on the modified interference pattern.

* * * * *